US00PP12405P2

(12) United States Plant Patent
Slaughter et al.

(10) Patent No.: US PP12,405 P2
(45) Date of Patent: Feb. 12, 2002

(54) PEACH TREE 'BURPEACHFOUR'

(75) Inventors: John K. Slaughter, Clovis; Timothy J. Gerdts, Kingsburg, both of CA (US)

(73) Assignee: The Burcehll Nursery, Inc., Oakdale, CA (US)

( * ) Notice: Subject to any disclaimer, the term of this patent is extended or adjusted under 35 U.S.C. 154(b) by 0 days.

(21) Appl. No.: 09/455,971

(22) Filed: Dec. 6, 1999

(51) Int. Cl.[7] ..... A01H 5/00
(52) U.S. Cl. ..... Plt./198

(58) Field of Search ..... Plt./198

*Primary Examiner*—Bruce R. Campell
*Assistant Examiner*—Susan B. McCormick
(74) *Attorney, Agent, or Firm*—Wells, St. John, Roberts, Gregory & Matkin, P.S.

(57) ABSTRACT

A new and distinctive variety of peach tree denominated varietally as Burpeachfour and which is characterized as to novelty by a date of maturity for commercial harvesting and shipment of approximately August 28 to September 8 under the ecological conditions prevailing in the San Joaquin Valley of central California.

1 Drawing Sheet

BACKGROUND OF THE NEW VARIETY

The present invention relates to a new, novel and distinct variety of peach tree which has been denominated varietally as 'Burpeachfour'. The 'Burpeachfour' Peach tree represents an exceptionally high quality, freestone peach which matures in late season. Another unique aspect of the 'Burpeachfour' is that it yields an exceptionally firm peach that exhibits a very high degree of external coloration as compared with the other freestone peach varieties which mature at approximately the same time.

ORIGIN AND ASEXUAL REPRODUCTION OF THE NEW VARIETY

The present peach tree variety was the result of an ongoing program of fruit and nut tree breeding. The purpose of this program is to improve the commercial quality of deciduous fruit and nut varieties and rootstocks by creating and releasing selections of prunus, malus and regia species. To this end, we make both controlled and hybrid crosses each year in order to produce seedling populations from which improved progenies are evaluated and selected.

The seedling 'Burpeachfour' was originated by the inventors in 1994, and selected from among a population of seedlings which were derived from a controlled cross of an unnamed peach seedling used as the pollen parent, and the 'Carnival' peach tree, (U.S. Plant Pat. No. 2,144), which was used as the seed parent. The resulting seed from this cross was planted in the spring of 1995. The new variety was selected from among seedlings growing in the experimental orchards of The Burchell Nursery, Inc. which is located near the city of Fowler, Calif., County of Fresno in the San Joaquin Valley. The seedling 'Burpeachfour' was marked for subsequent observation and noted as having exceptional characteristics. It was subsequently evaluated during the 1996–1999 fruit growing seasons. After the 1996 season, the seedling 'B2.034' was selected for advanced evaluation and repropagation.

The new variety 'Burpeachfour' was grafted onto two different and existing nemared peach rootstocks (unpatented) in February of 1997. Scionwood from the original seedling of the peach tree, 'Burpeachfour' was then collected and grafted onto the two peach rootstocks in the evaluation plot on the Burchell Nursery's experimental farm previously described. Fruit from the resulting propagation has been evaluated for both the 1998 and 1999 fruiting seasons. This subsequent evaluation clearly demonstrated that the repropagated trees are true to the characteristics of the original seedling in all observable aspects.

SUMMARY OF THE NEW VARIETY

The 'Burpeachfour' peach tree is characterized as to novelty and is otherwise noteworthy by producing fruit which ripens in late season; is considered very high quality; and which further is very firm and has an attractive coloration. In this regard, the present variety of peach tree bears fruit which are ripe for commercial harvesting and shipment approximately during the last days of August, that is, approximately 10 days before the commercial freestone peach tree variety 'Autumn Flame' (U.S. Plant Pat. No. 9,438) and which ripens during the time period of about September 5 to 10. Further, the present variety distinguishes itself from the variety 'Autumn Flame' by its high exterior coloration. Still further, the present variety, 'Burpeachfour', is distinguished from the 'Autumn Flame' peach tree by producing fruit which have an attractive reddish blush which covers approximately 70% to 80% of the exterior surface of the fruit, as compared to the fruit of the 'Autumn Flame' which is typically covered with a 40% to 60% blush.

BRIEF DESCRIPTION OF THE DRAWINGS

The accompanying drawing is a color photograph of a characteristic twig bearing typical leaves; several leaves showing both the dorsal and ventral coloration thereof; and several mature fruit showing their external coloration sufficiently matured for harvesting and shipment. Additionally, one fruit of the subject variety is dissected in the equatorial or cheek plane to illustrate the flesh and stone characteristics.

DETAILED DESCRIPTION

Referring more specifically to the pomological details of this new and distinct variety of peach tree, the following has been observed in 1998 and 1999 under the ecological conditions prevailing near the town of Fowler, county of Fresno, state of California. All major color code designations are by reference to the R.H.S. Colour Chart (Third Edition) provided by The Royal Horticultural Society of Great Britain.

Tree:

*Size.*—Generally considered average to above average as compared to other common peach cultivars.

*Productivity.*—Productive. Productivity with respect to pounds per acre is not availabe.

*Figure.*—The original seedling was trained in a central leader configuration with a moderate spread in the crown of the tree. The tree is considered upright to upright spreading in form.

*Height.*—The original seedling had a height dimension of 3.68 m at the end of the 1999 growing season.

*Width.*—The original seedling tree had a width of 1.88 m at the end of the 1999 growing season.

*Current season growth.*—The current season growth for the new variety was approximately 0.94–1.03 m.

*Regularity of bearing.*—Regular, and considered hardy under typical central San Joaquin Valley conditions.

Trunk:

*Diameter.*—Approximately 89 mm in diameter when measured at a distance of approximately 15.24 cm above the soil level. This was measured at the end of the 1999 growing season.

*Bark texture.*—Considered moderately rough. Numerous folds of papery scarf skin are normally present.

*Lenticels.*—Numerous, flat, oval lenticels are present. The lenticels range in size from approximately 3.0 to about 7.0 millimeters in width and from approximately 1 to about 2 millimeters in height.

*Lenticel color.*—RHS Greyed Orange Group 162 D.

*Bark coloration.*—Variable, but it is generally considered to be in a range of greyed orange (RHS Greyed Orange Group 177 A) to greyed-brown (RHS Greyed-Brown Group 197 A).

Branches:

*Size.*—Considered medium for the variety.

*Diameter.*—The branches have a diameter of about 52 mm when measured during the third year after grafting.

*Surface texture.*—Average, and appearing furrowed on wood which is several years old.

*Crotch angles.*—Variable between about 46° to 54° from the horizontal axis for scaffold limbs. This is not distinctive of the variety, however.

*Current season shoots.*—Surface Texture— Substantially glabrous.

*Internode length.*—Approximately 2.3 to 2.5 cm.

*Color of mature branches.*—Medium brown, (RHS Greyed Orange Group 201 C to 177 A).

*Current season shoots.*—Color— Light green, (RHS Yellow Green Group 145 B), with some reddish-brown coloration appearing on exposed exterior shoots, (RHS Greyed Red Group 181 B). The color of new shoot tips is considered a bright and shiny green, (RHS Green Group 143 B).

Leaves:

*Size.*—Considered relatively large for the species. All leaf measurements have been taken from vigorous upright current season growth at approximately mid-shoot.

*Leaf length.*—Approximately 169 to about 176 millimeters.

*Leaf width.*—Approximately 50 to about 52 millimeters.

*Leaf thickness.*—Approximately 1 to about 2 millimeters.

*Leaf base shape.*—The leaf base is slightly oblique.

*Leaf form.*—Lanceolate.

*Leaf tip form.*—Acuminate. The tip often appears flexed downwards and twisted laterally.

*Leaf color.*—Dark green, (RHS Green Group 137 B).

*Leaf texture.*—Substantially glabrous.

*Lower surface.*—Light green, (RHS Green Group 146 B).

*Venation.*—Pinnately net veined.

*Mid-vein.*—Color— Light yellow green, (RHS Yellow Green Group 150 D). Leaf Margins: Form— Considered crenate, occasionally doubly crenate. Uniformity— Considered generally uniform.

*Leaf petioles.*—Size— Considered medium. Length— Approximately 4 to 8 millimeters. Diameter— Approximately 1.5 to 2 millimeters. Color— Pale green, (RHS Yellow Green Group 150 B).

*Leaf glands.*—Size — Approximately 1 to 2 millimeters in height and 2 to 3 millimeters in width. Numbers— Generally 2–3 per side, occasionally one per side may be found. Type— Reniform. Color— Greenish brown, RHS Grey Brown 199 C.

*Leaf stipules.*—Size— Approximately 6–9 mm in length; 1 mm in width. Number—Typically 2 per leaf bud and up to 6 per shoot tip. Length— Approximately 6 to 9 millimeters. Form— Linear in form with a serrated margin. Color— Green (RHS Green Group 135 B) when young but changing to yellow-brown (RHS Greyed Orange Group 165 A) with advancing senescence. The stipules are considered to be early deciduous.

Flowers:

*Flower buds.*—Generally— The floral buds are considered to be medium in size, (21–24 mm long) and (14–17 mm wide); conic in form; and slightly appressed relative to the bearing shoot.

*Flower buds.*—Color— The bud scales are gray-brown, (approximately RHS Greyed Orange Group 177 C). The buds are considered hardy under typical central San Joaquin Valley climatic conditions.

*Hardiness.*—No winter injury has been noted during the several years of evaluation in the Central San Joaquin Valley. The current variety has not been intentionally subjected to drought or heat stress and therefore this information is not available.

*Blooming type.*—Considered average in relative comparison to other peach cultivars commonly growing in the central San Joaquin Valley. Date of full bloom was March 9, in 1998.

*Flower type.*—The variety is considered to be a showy type flower.

*Flower size.*—Flower diameter at full bloom is approximately 38 to 42 millimeters.

*Bloom quantity.*—Considered abundant.

*Flower bud frequency.*—Normally 1 to 2 buds appear per node.

*Petal size.*—Generally— Considered medium for the species. Length— Approximately 19 to 21 millimeters. Width— Approximately 16 to 18 millimeters.

*Petal shape.*—Broadly ovate.

*Petal count.*—Nearly always 5.

*Petal texture.*—Glabrous.

*Petal color.*—Light pink when young, (approximately RHS Red Purple Group 62 D), and darkening with advancing senesence to a medium pink, (RHS Red Purple Group 67 C). The lower portion of the flower petal is typically darker than the apical portions and exhibits medium pink coloration (RHS Red Purple 62 B).

*Fragrance.*—None to occasionally slight.

*Petal claw.*—Form— The claw is considered truncate in shape and has a medium size when compared to other similar varieties. Length— Approximately 1.5 to 2.1 millimeters. Width— Approximately 1 millimeter.

*Petal margin.—Generally— Considered variable, from nearly smooth, to highly undulate and ruffled, especially apically.*

*Petal apex.*—Generally— The petal apices appear slightly domed.

*Flower pedicel.*—Length— Considered medium-short, and having an average length of approximately 1.4 to 1.8 millimeters. Diameter— Considered average, approximately 1 millimeter. Color— Bright green, (RHS Yellow Green Group 144 C).

*Floral nectaries.*—Color— Dull, orange, orange-gold, (approximately RHS Orange Group 25 B). The color of the nectaries become increasingly dull and slightly darker with advancing senescence.

*Calyx.*—Surface Texture— Generally glabrous. Color— A dull red (approximately RHS Greyed Red Group 181 B).

*Sepals.*—Surface Texture— The surface has a medium length, wooly, and gray (RHS Greyed Green Group 198 D) colored pubescence. Number— Generally 5 per flower. Size— Typically 4–5 mm wide and 5–6 mm long and ovate in form. Color— A dull red, (approximately RHS Greyed Red Group 182 B).

*Anthers.*—Generally— Average in size, approximately 1.0 mm in length and 1.0–1.5 mm in width. Color— Red to reddish-orange dorsally, (approximately RHS Greyed Purple Group 184 B). Pollen Production— Pollen is abundant, and has a yellow-gold color, (approximately RHS Yellow Orange 19 A).

*Filaments.*—Size— Variable in length, approximately 12 to 16 millimeters. Color— White, (RHS Red Purple Group 69 D), and darkening with advanced maturity.

*Pistil.*—Generally— Average in size. Length— Approximately 15 to 17 millimeters, including the ovary. Color— Considered a very pale green when young, approximately (RHS Yellow Green Group 150 D), and becoming slightly more yellowish with advancing senescence. Surface Texture— Pubescent.

Fruit:

*Maturity when described.*—The present variety of plant is described, as it would be found, at full commercial maturity. In this regard, the fruit of the present variety was first picked on Aug. 28th, 1998. The date of last pick of the same variety (in 1998) was approximately September 8th under the ecological conditions prevailing in the San Joaquin Valley of central California.

*Size.*—Generally— Medium large, and considered uniform.

*Average cheek diameter.*—Approximately 76 to 79 millimeters.

*Average suture diameter.*—Approximately 73 to 77 millimeters.

*Average axial diameter.*—Approximately 78 to 82 millimeters.

*Fruit weight.*—Typical weight 178 grams. This is highly dependent on cultural practices, and therefore is not distinctive of the present variety.

*Fruit form.*—Generally— Oblate in its lateral aspect. The fruit is generally uniform in symmetry. The fruit has a slightly oval form when viewed from the apical aspect.

*Fruit suture.*—Generally— The suture appears as a thin line which extends from the base to the apex, and appears slightly deeper, basally, within the stem well, and apically on both sides of the pistil point. No apparent callousing or stitching exists along the suture line.

*Suture.*—Color— The suture normally is the same color as the underlying blush. This is variable, from an orange-yellow background color, (RHS Yellow Group 13 D), to a red orange color, (RHS Red Group 46 A).

*Ventral surface.*—Form— Considered uniform.

*Stem cavity.*—Size: Considered moderately shallow for the species. Width: Approximately 9–13 millimeters.

*Length.*—Approximately 22–27 millimeters.

*Depth.*—Approximately 6 to 9 millimeters.

*Form.*—Considered narrowly oval.

*Fruit base.*—Generally— Considered truncate in form, and uniform.

*Fruit apex.*—Generally— Considered depressed and usually recessed below the height of the apical shoulders.

*Fruit stem.*—Generally— Considered medium in length, approximately 7 to 9 millimeters. Diameter— Approximately 3 to 4 millimeters. Color— Generally a pale yellow-green, (approximately RHS Yellow Green Group 145 B).

*Fruit skin.*—Generally— Considered average in thickness. Surface Texture— The variety has a very light, short pubescence. Skin Acidity— Considered neutral.

*Tenacious to flesh.*—Yes at commercial maturity.

*Tendency to crack.*—Not observed.

*Skin color.*—Generally— Variable, approximately 70% to 80% of the fruit surface is covered with an attractive red blush.

*Blush color.*—The blush color is generally more prevalent apically. This red blush color ranges from a dark red, (RHS Red Group 46A) to red, (RHS 47C), with many degrees of shading and blending between these colorations.

*Skin ground color.*—This is generally present in variable percentages covering approximately 20% to 30% of the fruit surface, and which is a Yellow-golden color, (RHS Yellow Orange Group 22A to 20D).

*Flesh color.*—Generally— Considered variable, from a yellow/orange, (RHS Yellow Orange Group 16A to 16D), to reddish orange, (approximately RHS Red Group 45B). This color can radiate into the flesh generally beginning at the exterior margin.

*Flesh fibers.*—Generally— Present. These fibers are numerous and light colored. These fiber are present throughout the flesh.

*Stone cavity.*—Color— Red, (approximately RHS Red Group 45B), to a yellow orange, (approximately RHS Yellow Orange Group 18 B). With increasing maturity, occasional red flecks can appear randomly in the flesh. These flecks are somewhat lighter in color than the surface of the stone cavity.

*Flesh texture.*—Generally— The flesh is considered firm and fine at commercial maturity.

*Ripening.*—Generally— The fruit of the present variety ripens evenly.

*Flavor.*—Considered very sweet and mildly acidic. The flavor is considered both pleasant and balanced.

*Aroma.*—Pleasant and abundant.

*Eating quality.*—Generally— Considered very good to excellent, and well above average when compared with other common peach varieties.

Stone:

*Attachment.*—Generally— The stone is considered completely freestone at commercial maturity.

*Stone size.*—Generally— Considered medium to medium-small for the variety and the date of harvesting of same.

*Length.*—Approximately 34 to 36 millimeters.

*Width.*—Approximately 27 to 29 millimeters.

*Diameter.*—Approximately 20 to 22 millimeters.

*Fibers.*—Generally— A few medium length fibers are attached along the entire surface of the stone.

*Stone form.*—Generally— The stone is considered oval.

*Stone base.*—The stone base is somewhat oblique.

*Base angle.*—The base angle of the stone is variable, but, most frequently is considered slightly oblique to the stone axis.

*Hilum.*—Generally— Considered medium in size, and relatively well defined. The hilum is approximatly 5 to 6 millimeters long, and approximately 3 to 4 millimeters wide. Form— considered oval.

*Apex.*—Shape— the stone apex is raised and has an acute tip.

*Stone shape.*—Considered variable. The stone is normally unequal although occasionally it may appear nearly equal.

*Stone surface.*—Surface Texture— Generally considered medium in roughness. The stone exhibits substantial pitting laterally. Substantial grooving is apparent over the apical shoulders. Surface pitting is prominent and occurs more frequently present basally. Ridges— Numerous fine ridges are present basally and converge towards the base of the stone.

*Ventral edge.*—Width— Considered medium, and having a dimension of approximately 5.0 to 6.5 millimeters at approximately mid-suture with the wings being most prominent over the basal area.

*Dorsal edge.*—Full, heavily grooved and having jagged edges. The dorsal edge is moderately eroded over the apical shoulder.

*Stone color.*—The color of the dry stone is a light to medium brown, (RHS Orange Red Group 34 D).

*Tendency to split.*—No splitting noted.

*Kernel.*—Form— Oval. Length— 22–24 mm. Width— 16–18 mm. Thickness— 3–5 mm. Pellicle— Slight pubescence noted. Color— RHS Greyed-Orange Group 173B.

*Use.*—The subject variety Burpeachfour is considered to be a late maturing, very firm, highly attractive colored peach which finds value in both local and long distance shipping.

*Keeping quality.*—Fruit has stored well up to 20 days after harvest at temperatures of about 2.0° C.

*Resistance to insects and disease.*—No particular susceptibilities were noted.

*Shipping quality.*—Well above average.

Although the new variety of Peach Tree possesses the described characteristics as a result of the growing conditions prevailing in Fresno County, Calif, in the central part of the San Joaquin Valley, it is to be understood that variations in the usual magnitude and characteristics incident to growing conditions, fertilization, pruning and pest control are to be expected.

Having thus described and illustrated our new variety of Peach Tree, what is claimed as new and desired to be secured by PLANT LETTERS PATENT is:

1. A new and distinct variety of Peach Tree substantially as illustrated and described, and which is denominated varietally as Burpeachfour and which further is characterized principally as to novelty by providing fruit which is ripe for harvesting and shipment from about August 28 to about September 8 under the ecological conditions prevailing in the San Joaquin Valley of Central California.

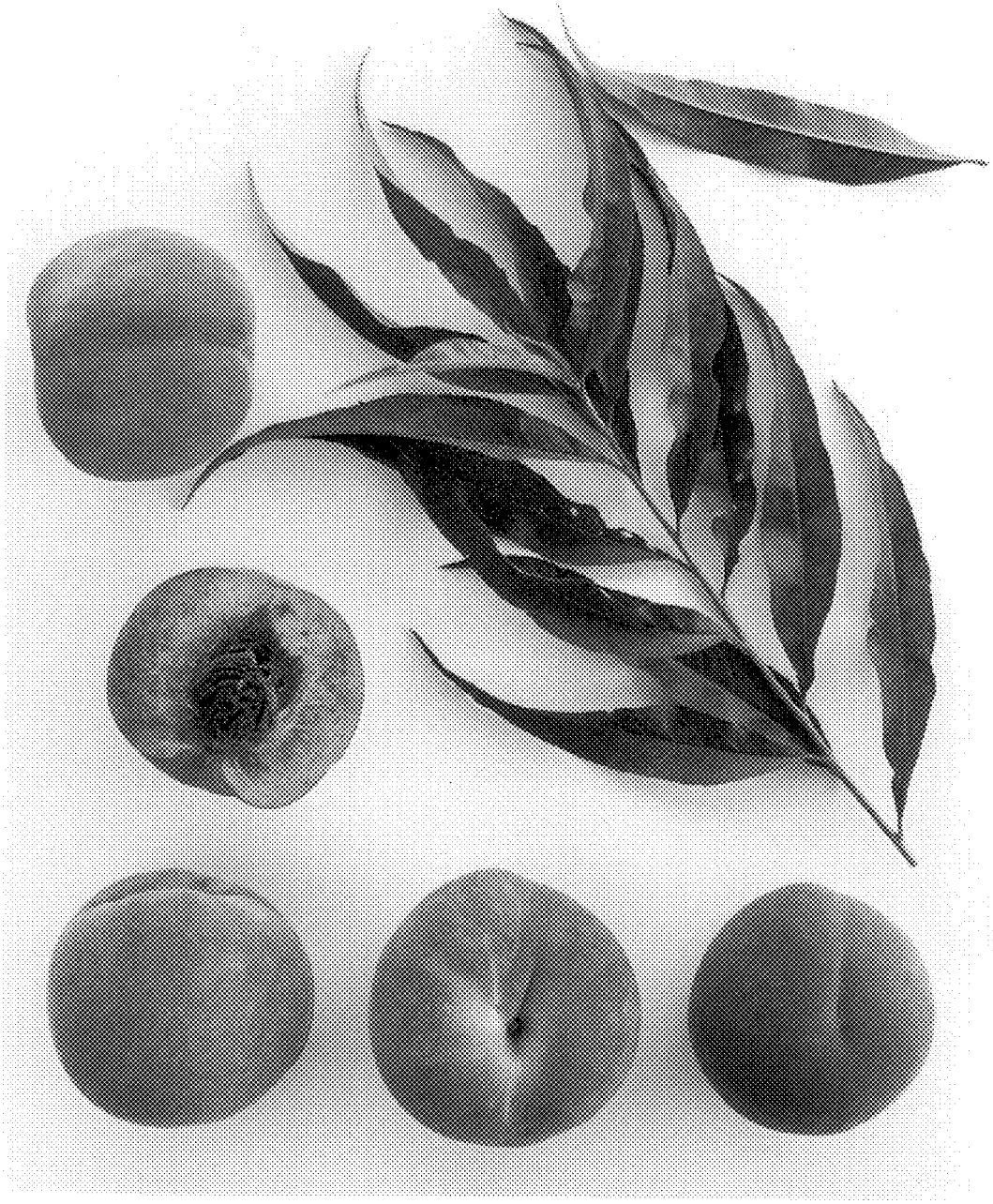

* * * * *